(12) United States Patent
Kumar

(10) Patent No.: US 12,161,878 B1
(45) Date of Patent: Dec. 10, 2024

(54) WEARABLE DEVICE FOR BIORESONANCE MODULATION OF MUSCLE TEMPERATURE AND BLOOD OXYGEN LEVELS

(71) Applicant: Healing Anywhere LLC, Austin, TX (US)

(72) Inventor: Bharat Kumar, Austin, TX (US)

( * ) Notice: Subject to any disclaimer, the term of this patent is extended or adjusted under 35 U.S.C. 154(b) by 0 days.

(21) Appl. No.: 18/407,372

(22) Filed: Jan. 8, 2024

(51) Int. Cl.
*A61N 2/00* (2006.01)

(52) U.S. Cl.
CPC ..................... *A61N 2/004* (2013.01)

(58) Field of Classification Search
CPC ...................................................... A61N 2/004
See application file for complete search history.

(56) References Cited

U.S. PATENT DOCUMENTS

| | | | | |
|---|---|---|---|---|
| 5,706,805 | A * | 1/1998 | Swartz | G01R 33/60 600/431 |
| 9,658,651 | B2 * | 5/2017 | Balogh | H04M 1/724092 |
| 2007/0156040 | A1 * | 7/2007 | Mouradian | A61B 5/14532 600/365 |
| 2009/0187232 | A1 * | 7/2009 | Salim | A61N 1/40 600/407 |
| 2014/0128941 | A1 * | 5/2014 | Williams | H05B 45/00 315/193 |
| 2017/0007847 | A1 * | 1/2017 | Gross | A61M 21/02 |
| 2023/0239618 | A1 * | 7/2023 | Lee | G06V 30/40 381/56 |
| 2023/0392172 | A1 * | 12/2023 | Liu | C12M 21/12 |

\* cited by examiner

*Primary Examiner* — Akm Zakaria
(74) *Attorney, Agent, or Firm* — Mertzlufft Law PLLC; Joshua D. Mertzlufft, Esq.

(57) ABSTRACT

A wearable system is disclosed, which may include a housing containing a processor, a network interface, a temperature sensor, an optical sensor, and an electromagnetic frequency generator. The system may further include a band connected to the housing for securing it to a user. The processor may be configured to receive muscle temperature and blood oxygen level data from the sensors, transmit the data to a remote device via the network interface, receive a bioresonance modality instruction from the remote device, instruct the electromagnetic frequency generator to emit an electromagnetic bioresonance frequency based on the instruction, and transmit updated muscle temperature and blood oxygen level data to the remote device. The system may enable remote monitoring and control of bioresonance to encourage the user's bioresonance state.

20 Claims, 6 Drawing Sheets

WEARABLE DEVICE FOR BIORESONANCE MODULATION OF MUSCLE TEMPERATURE AND BLOOD OXYGEN LEVELS

BACKGROUND

Wearable health technology generally relates to electronic devices that consumers can wear, like smartwatches and fitness trackers, which are designed to collect data regarding the user's health and exercise. The data collected can include heart rate, sleep patterns, steps walked, calories burned, and other health metrics. The appeal of wearable technology lies in its ability to provide real-time health monitoring and data analysis, which can potentially assist users in making informed decisions about their health and lifestyle. However, wearable health technology is typically limited to data monitoring, not acting on the user.

Bioresonance explores the use of electromagnetic waves at specific frequencies to alter the body's bioresonance activity. Active bioresonance is based on a variety of concepts, including the concept that unhealthy cells or organs emit altered electromagnetic waves due to DNA damage or other causes.

SUMMARY

This Summary is intended to introduce, in an abbreviated form, various topics to be elaborated upon below in the Detailed Description. This Summary is not intended to identify key or essential aspects of the claimed invention. This Summary is similarly not intended for use as an aid in determining the scope of the claims.

In some aspects, the techniques described herein relate to a system, including: a wearable device configured to be worn by a user, the wearable device including: a housing having disposed therein: a processor, a network interface in electronic communication with the processor, a temperature sensor in electronic communication with the processor and configured to sense a muscle temperature, an optical sensor in electronic communication with the processor and configured to sense a blood oxygen level, and an electromagnetic frequency generator in electronic communication with the processor; and a band connected to the housing and configured to removably secure the housing to the user such that the electromagnetic frequency generator is positioned to act on the user; wherein the processor is configured to perform a method including: receiving, at the processor, a first muscle temperature from the temperature sensor and a first blood oxygen level from the optical sensor; sending, from the processor, via the network interface, the first muscle temperature and the first blood oxygen level to a remote device; receiving, at the processor, from the remote device, a selected bioresonance modality instruction, the selected bioresonance modality instruction including an instruction to emit an electromagnetic bioresonance frequency from the electromagnetic frequency generator; instructing the electromagnetic frequency generator to emit the electromagnetic bioresonance frequency according to the bioresonance modality instruction; receiving, at the processor, a second muscle temperature from the temperature sensor and a second blood oxygen level from the optical sensor; and sending, from the processor, via the network interface, the second muscle temperature and the second blood oxygen level to the remote device.

In some aspects, the techniques described herein relate to a system, wherein the wearable device is configured to be worn on a wrist of the user.

In some aspects, the techniques described herein relate to a system, wherein the wearable device is configured to be worn on an ankle of the user.

In some aspects, the techniques described herein relate to a system, wherein the network interface is a BLUETOOTH network interface.

In some aspects, the techniques described herein relate to a system, wherein the remote device includes an electronic storage device having a database stored thereon, the database including a plurality of bioresonance modality instructions including the selected bioresonance modality instruction.

In some aspects, the techniques described herein relate to a system, wherein the selected bioresonance modality instruction is selected on the remote device from the plurality of bioresonance modality instructions.

In some aspects, the techniques described herein relate to a system, wherein the remote device is configured to download a downloadable bioresonance modality instruction and add the downloadable bioresonance modality instruction to the plurality of bioresonance modality instructions.

In some aspects, the techniques described herein relate to a system, wherein the processor is further configured to change the bioresonance frequency based on one or more of the first muscle temperature, the second muscle temperature, the first blood oxygen level, or the second blood oxygen level.

In some aspects, the techniques described herein relate to a method, including: providing a wearable device configured to be worn by a user, the wearable device including: a housing having disposed therein: a processor, a network interface in electronic communication with the processor, a temperature sensor in electronic communication with the processor and configured to sense a muscle temperature, an optical sensor in electronic communication with the processor and configured to sense a blood oxygen level, and a frequency generator in electronic communication with the processor; and a band connected to the housing and configured to removably secure the housing to the user such that the frequency generator is positioned to act on the user; receiving, at the processor, a first muscle temperature from the temperature sensor and a first blood oxygen level from the optical sensor; sending, from the processor, via the network interface, the first muscle temperature and the first blood oxygen level to a remote device; receiving, at the processor, from the remote device, a selected bioresonance modality instruction, the selected bioresonance modality instruction including an instruction to emit a bioresonance frequency from the frequency generator; instructing the frequency generator to emit the bioresonance frequency according to the bioresonance modality instruction; receiving, at the processor, a second muscle temperature from the temperature sensor and a second blood oxygen level from the optical sensor; and sending, from the processor, via the network interface, the second muscle temperature and the second blood oxygen level to the remote device.

In some aspects, the techniques described herein relate to a method, wherein the frequency generator is an electromagnetic frequency generator and the bioresonance frequency is an electromagnetic frequency.

In some aspects, the techniques described herein relate to a method, wherein the wearable device is configured to be worn on a wrist or an ankle of the user.

In some aspects, the techniques described herein relate to a method, wherein the network interface is a Bluetooth network interface.

In some aspects, the techniques described herein relate to a system, including: a wearable device, the wearable device including: a housing having disposed therein: a processor, a network interface in electronic communication with the processor, a temperature sensor in electronic communication with the processor and configured to sense a muscle temperature, an optical sensor in electronic communication with the processor and configured to sense a blood oxygen level, and a frequency generator in electronic communication with the processor; wherein the processor is configured to perform a method including: receiving, at the processor, a first muscle temperature from the temperature sensor and a first blood oxygen level from the optical sensor; sending, from the processor, via the network interface, the first muscle temperature and the first blood oxygen level to a remote device; receiving, at the processor, from the remote device, a selected bioresonance modality instruction, the selected bioresonance modality instruction including an instruction to emit a bioresonance frequency from the frequency generator; and instructing the electromagnetic frequency generator to emit the bioresonance frequency according to the bioresonance modality instruction.

In some aspects, the techniques described herein relate to a system, wherein the method the processor is configured to perform further includes: receiving, at the processor, a second muscle temperature from the temperature sensor and a second blood oxygen level from the optical sensor; and sending, from the processor, via the network interface, the second muscle temperature and the second blood oxygen level to the remote device.

In some aspects, the techniques described herein relate to a system, wherein the processor is further configured to change the bioresonance frequency based on one or more of the first muscle temperature, the second muscle temperature, the first blood oxygen level, or the second blood oxygen level.

In some aspects, the techniques described herein relate to a system, wherein the wearable device further includes a band connected to the housing and configured to removably secure the housing to a user such that the frequency generator is positioned to act on the user.

In some aspects, the techniques described herein relate to a system, wherein the frequency generator is an electromagnetic frequency generator and the bioresonance frequency is an electromagnetic frequency.

In some aspects, the techniques described herein relate to a system, wherein the network interface is a BLUETOOTH network interface.

In some aspects, the techniques described herein relate to a system, wherein the remote device includes an electronic storage device having a database stored thereon, the database including a plurality of bioresonance modality instructions including the selected bioresonance modality instruction.

In some aspects, the techniques described herein relate to a system, wherein the selected bioresonance modality instruction is selected on the remote device from the plurality of bioresonance modality instructions.

BRIEF DESCRIPTION OF THE FIGURES

For a fuller understanding of the nature and objects of the disclosure, reference should be made to the following detailed description taken in conjunction with the accompanying drawings, in which.

DETAILED DESCRIPTION

Figure 1A:
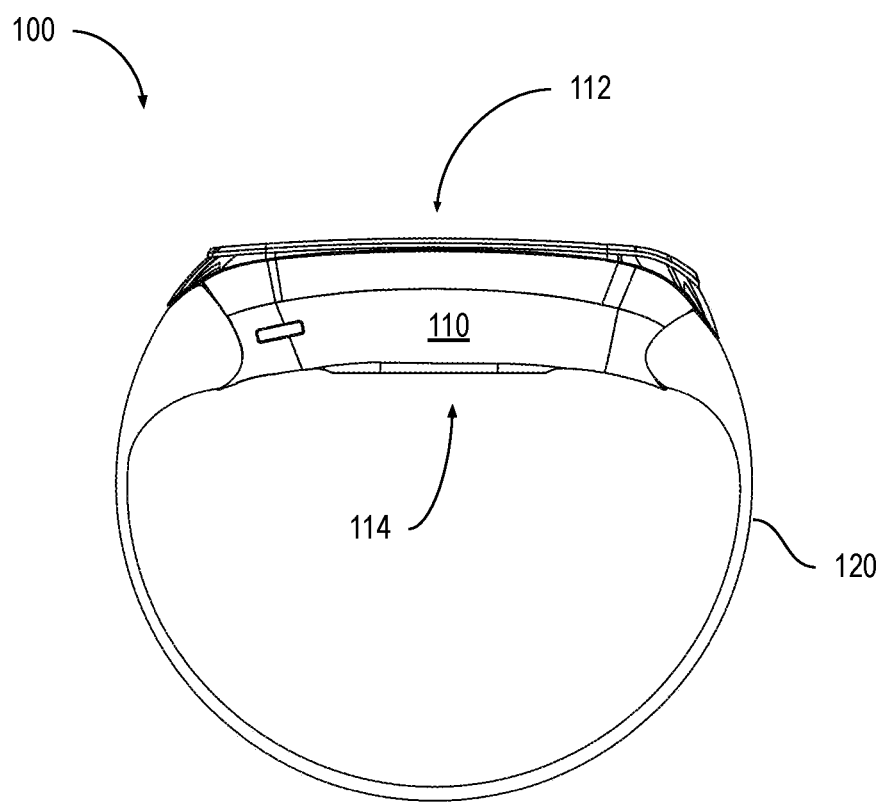
FIG. 1A illustrates a wearable device, according to one or more implementations herein.

It is to be understood that the invention is not limited in its application to the details of construction and the arrangements of components and/or method steps set forth in the following description or illustrated in the drawings, and phraseology and terminology used herein is for the purpose of description and should not be regarded as limiting. The invention is capable of other embodiments and of being practiced or being carried out in various ways. Accordingly, other aspects, advantages, and modifications will be apparent to those skilled in the art to which the invention pertains, and these aspects and modifications are within the scope of the invention, which is limited only by the appended claims.

Implementations herein include systems and methods for providing dynamic and responsive bioresonance modalities and obtaining real-time physiological data from a user. Implementations provide for seamless communication between a non-invasive wearable device and a remote system for the purpose of receiving updated bioresonance modality instructions for implementing bioresonance modalities for the user. Implementations offer the convenience of being worn on various parts of the body. Therefore, implementations herein address deficiencies of conventional non-drug-based solutions by providing personalized, adaptable, and convenient systems for delivering bioresonance modalities.

A conventional solution may include physical therapy sessions designed to improve patient mobility and manage pain through a series of exercises and therapeutic techniques. Physical therapy sessions typically involve a series of exercises and treatments designed to address specific musculoskeletal conditions. These sessions are conducted by a trained physical therapist who assesses the patient's mobility, strength, and pain levels to tailor a treatment plan that may include manual therapy techniques, such as massage and joint mobilization, to improve movement and reduce discomfort. Additionally, prescribed exercises are often employed to strengthen muscles, improve coordination, and increase flexibility. The use of equipment such as resistance bands, weights, and exercise machines may be incorporated to aid in the rehabilitation process. The therapist also educates patients on proper body mechanics and posture to prevent further injury. Progress may be regularly monitored and the treatment plan may be adjusted as the patient's condition improves, with the goal of restoring optimal physical function over time.

However, physical therapy sessions may lack precise and consistent measurement of patients' progress due to a reliance on subjective evaluations or manual measurements, which can lead to suboptimal treatment adjustments. Additionally, the need for patients to travel to a clinic can result in inconsistent attendance, especially for those with mobility issues or in remote areas. The limited availability of therapists may also cause delays in treatment, potentially slowing down a patient's recovery process. Furthermore, in-clinic therapy equipment may be typically static and may not be tailored to the specific needs or progress of an individual, thus not providing the most efficient or effective rehabilitation experience.

A further conventional solution may include standard biofeedback devices that may monitor physiological responses and provide feedback to users, enabling them to gain voluntary control over certain bodily functions. Standard biofeedback devices operate by monitoring physiological signals from the body, such as heart rate, skin conductivity, muscle tension, and brainwave activity, among others. These signals may be captured via sensors that are attached to the user's body. The data collected by these sensors may then be conveyed to a processing unit, which interprets the signals and provides feedback to the user. The feedback may be commonly presented in a form that the user can easily understand, such as visual displays or audio cues, allowing individuals to become aware of their physiological responses and to potentially control them through conscious adjustments.

However, standard biofeedback devices often face challenges in providing real-time, accurate feedback due to limitations in sensor technology or data processing capabilities. These devices may struggle with delays in feedback delivery, which can diminish the efficacy of biofeedback training by preventing timely adjustments from the user. Furthermore, conventional devices might not offer sufficient customization for different users or adaptability to various environmental conditions, potentially leading to less accurate readings or a decrease in user comfort. Additionally, the user interface of these devices may not be intuitive, making it difficult for users to interpret the data and take appropriate action. The inability of these devices to seamlessly integrate into the user's lifestyle or work environment can also lead to decreased usage and engagement, thus undermining the potential benefits of biofeedback training.

A further conventional solution may include a temperature-modulating pack, which may be capable of being cooled or heated to provide relief from various types of discomfort. Traditional cold and heat packs generally consist of a sealed container or pouch that holds a temperature-retentive substance or a chemical reactant. For cold applications, the substance within the pouch might be a gel that remains pliable even when frozen, allowing the pack to conform to the contours of the body. Upon freezing, the gel absorbs a significant amount of heat from its surroundings, thereby providing a sustained cold temperature. Heat packs, in contrast, might contain a supersaturated solution of sodium acetate or similar chemicals. Upon activation, typically by flexing a small metal disc inside the pack, the solution crystallizes exothermically, releasing heat. Alternatively, heat packs may contain substances like iron powder, activated carbon, and salt, which, when exposed to air, oxidize in a reaction that generates heat. These heat packs are single-use and rely on the exothermic reaction of the iron when it rusts.

However, traditional cold and heat packs are limited in their ability to maintain the desired therapeutic temperature over an extended period. These packs often require refrigeration or microwaving to reach the appropriate cold or hot state, yet they tend to quickly deviate from the optimal temperature range, reducing their efficacy. The materials used in these packs can also be prone to leakage or rupture, and the temperature they deliver may not be evenly distributed, leading to potential discomfort or even injury to the skin. Moreover, the inability to precisely control the temperature of these packs limits their usefulness for various medical conditions that require specific and sustained temperature treatments.

Implementations herein may solve some or all of the shortcomings by providing a wearable device that includes a variety of sensors and components integrated into a housing. This wearable device may be equipped with a processor, a network interface for communication, a temperature sensor that measures muscle temperature, an optical sensor that measures blood oxygen levels, and a frequency generator capable of emitting bioresonance frequencies.

The processor within the wearable device may be responsible for executing several tasks. It may collect data such as muscle temperature and blood oxygen levels from the respective sensors. The processor may also direct the frequency generator to emit a bioresonance frequency in accordance with instructions stored on the wearable device or received from an external user device. The wearable device can be worn on different parts of the user's body such as the wrist or ankle. Additionally, the device may be capable of updating the bioresonance frequency emitted by the frequency generator either based on instructions internally or those received from an external user device.

Implementations are distinguished from traditional solutions by offering a dynamic and personalized approach to bioresonance modality. Unlike standard biofeedback devices that merely display information to the user, the wearable device actively emits bioresonance frequencies. This contrasts with the static nature of physical therapy sessions, which require the presence of a healthcare professional. Additionally, the system offers a more sophisticated solution compared to generic cold and heat packs, which provide a one-dimensional approach to muscle therapy. Furthermore, the integration of a network interface allows the system to communicate with a remote device, enhancing its functionality beyond the capabilities of conventional solutions by enabling updates, customization, and a broader range of bioresonance modalities to be employed as part of the user's bioresonance regimen.

FIG. 1A illustrates a wearable device 100, according to one or more implementations herein. Wearable devices may refer to devices designed to be worn by an individual that incorporate one or more sensors, processors, network interfaces, and frequency generators. Such a device may be tailored to conform to various parts of the human body, such as the wrist or ankle, allowing for continual monitoring and interaction with the user's physiological state. The sensors integrated into such devices may include, but are not limited to, a temperature sensor for detecting muscle temperature and an optical sensor for measuring blood oxygen levels. The processor serves the function of analyzing the data collected by these sensors and communicating with a remote device via the network interface, which may utilize wireless communication protocols such as BLUETOOTH. The frequency generator, which may be an electromagnetic frequency generator, may be configured to emit bioresonance frequencies corresponding to instructions stored on the wearable device 100 or received from the remote device. These frequencies may be adjusted based on the physiological data collected, thereby providing a personalized bioresonance experience. The wearable device 100 may be not only portable but also may be capable of delivering bioresonance modality (e.g., to modulate the user's bioresonance) in a manner that may be responsive to the real-time physiological conditions of the user.

The wearable device 100 may comprise a housing 110 and a band 120. The housing 110 may include a protective casing or enclosure that may be designed to contain and support various components of the wearable device 100, such as processors, sensors, frequency generator, and network interface. The housing 110 may be constructed to be durable and comfortable for the user when worn on the body, potentially against the skin or over clothing. It may be fashioned from materials that are lightweight, hypoallergenic, and resistant to environmental factors such as moisture, dust, and temperature fluctuations. The housing 110 serves not only to protect the internal components from physical damage and environmental conditions but also to provide a means for securing the device to the user's body and to facilitate the proper positioning and functioning of the sensors and the frequency generator in relation to the user's physiological parameters. The design and shape of the housing 110 may be tailored to conform to the contours of the body part on which it may be intended to be worn, such as the wrist or ankle, to ensure consistent readings and comfort during use. Additionally, the housing 110 may include user interface elements such as buttons, touchscreens, or indicator lights, providing the user with the capability to interact with the device or receive feedback regarding the status or operation of the wearable device 100.

The housing 110 may include a top face 112 and a bottom face 114. The top face 112 may, in some implementations, include a display or other indicator. The bottom face 114 may include one or more sensors and/or emitters.

The band 120 may refer to a structural component of the wearable device 100 that may be configured to secure the wearable device 100 to a user's body. The band 120 may be constructed from flexible materials such as silicone, rubber, fabric, or other suitable polymers to provide comfort and adaptability to various body parts and sizes. It may also include an adjustable fastening mechanism, such as a buckle, clasp, or hook-and-loop fastener, to enable the user to snugly fit the wearable device around the targeted area such as the wrist, arm, or ankle. The band 120 may further incorporate channels or housings for the integration of sensors and the frequency generator, maintaining their positions relative to the skin to ensure accurate data collection and effective frequency emission. Additionally, the design of the band 120 may allow for the easy removal or replacement of the housing 110 or other components of the wearable device 100 for maintenance or charging purposes.

The band 120 may be, in some implementations, configured to provide for a user to secure the wearable device 100 to the user's wrist (e.g., the region of a user's body where the forearm meets the hand, typically characterized by the presence of the carpal bones and the associated complex of joints and ligaments that allow for the articulation and range of motion of the hand). This area may be commonly used as a site for wearable devices due to its accessibility and the ability to obtain physiological data relevant to the user's health and wellness, such as pulse rate or blood oxygenation. In the context of the wearable technology described, the wrist may serve as a potential location for the device to be securely positioned in order to monitor, analyze, and respond to physiological signals with the aim of delivering bioresonance modality tailored to the user's needs. However, it should be understood that implementations of the wearable device 100 may be configured for attachment to various other portions of a user's body (e.g., arm or ankle).

Figure 1B:
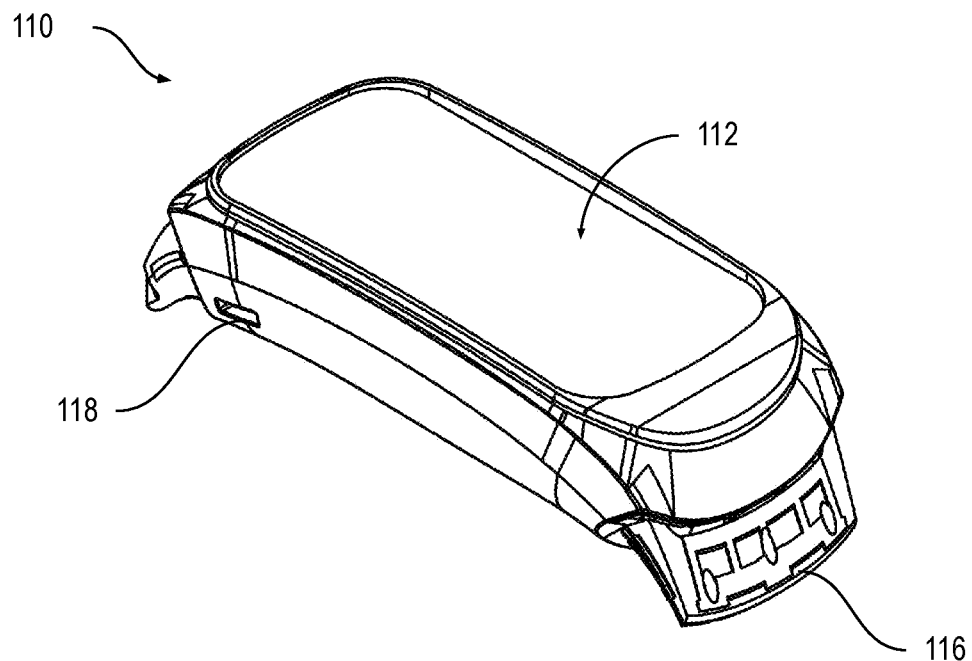
FIG. 1B illustrates a top isometric view of the housing of the wearable device, according to one or more implementations herein.

FIG. 1B illustrates a top isometric view of the housing 110 of the wearable device, according to one or more implementations herein.

The housing 110 may include the top face 112. The top face 112 may be configured with one or more displays or indicators, or may be blank. The housing 110 may further include one or more band connectors 116. The band connectors 116 may be configured for permanent or removable attachment of the band 120 to the housing 110. The housing 110 may further include a port 118. The port 118 may be one of a variety of types of electronic ports, for example, universal serial bus (USB), or other type of electronic port. The port 118 may be configured for one or more of charging, programming, and data transmission to and from the wearable device 100.

Figure 1C:
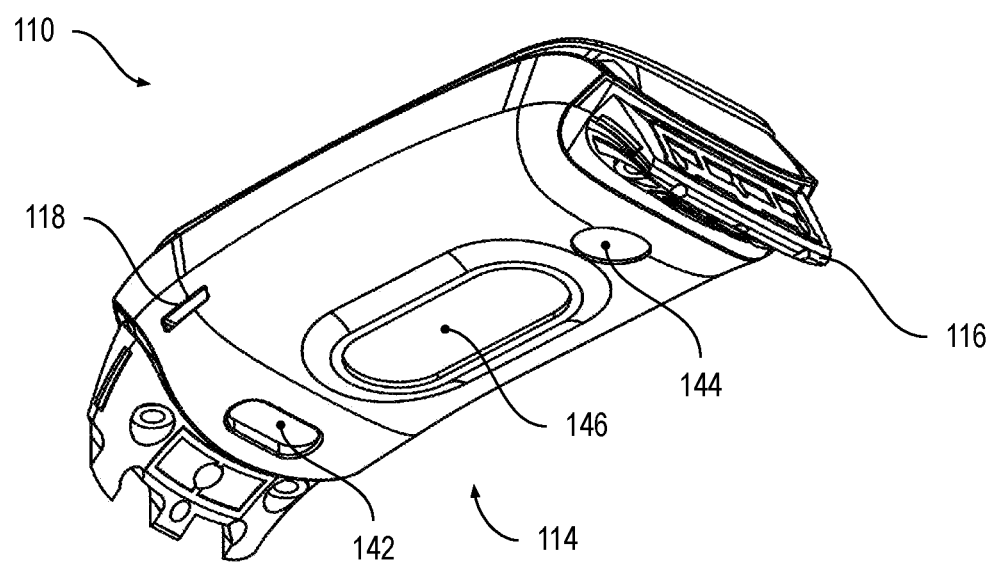
FIG. 1C illustrates a bottom isometric view of the housing of the wearable device, according to one or more implementations herein.

FIG. 1C illustrates a bottom isometric view of the housing 110 of the wearable device, according to one or more implementations herein.

The housing 110 may include the bottom face 114. Within or proximate the bottom face 114 may be one more sensors or emitters of the wearable device 100. For example, the bottom face 114 may include proximate thereto a temperature sensor 142, an optical sensor 144, and a bioresonance frequency emitter 146. It will be understood that the locations, orders, shapes, and sizes of the temperature sensor 142, the optical sensor 144, and the bioresonance frequency emitter 146 are not limited to those illustrated in FIG. 1C.

The temperature sensor 142 may refer to a device or component that detects and measures thermal energy emanating from a user's muscles, converting this energy into a data signal. The temperature sensor 142 may be based on thermocouple, resistive temperature detector (RTD), thermistor, semiconductor-based integrated circuit (IC) technology, infrared, or any other suitable temperature sensing technology that provides accurate and reliable readings of muscle temperature. The temperature sensor 142 may be in direct or indirect contact with the user's skin in order to capture precise temperature readings, and these readings may be utilized by the processor within the wearable device to monitor the user's physiological state or to adjust the output of the bioresonance frequency generator accordingly.

The temperature sensor 142 may be configured in some implementations to monitor a user's muscle temperature, for example, a localized thermal readings from the muscle tissue of a user, which may be indicative of the metabolic activity and the state of the muscle. These readings can be taken at or near the surface of the skin overlaying the muscle or within the muscle tissue itself. Temperatures may be measured at various depths of muscle tissue and may include the core temperature of the muscle as well as temperatures closer to the muscle's surface. The data obtained from such measurements may be used to analyze the user's physiological condition, exercise intensity, potential for muscle strain or injury, recovery status, or other health-related insights. Muscle temperatures may also encompass the average temperature across a targeted muscle group or specific point measurements from a single muscle.

The optical sensor 144 (e.g., a pulse oximeter) may refer to a device capable of detecting light and converting it into an electronic signal for measurement or analysis. The optical sensor 144 may operate by emitting light, such as infrared or visible spectrum light, towards the area of interest, such as the skin or a blood vessel, and then measuring the intensity of the light that may be either reflected back from the target or transmitted through it. The data obtained from this interaction may be used to determine various physiological parameters, including but not limited to, the blood oxygen level (e.g., the concentration of oxygen that may be present in the bloodstream, which may be typically measured as a percentage of oxygen-saturated hemoglobin relative to the total hemoglobin in the blood), heart rate, or other characteristics related to the blood's properties or the skin's condition.

The optical sensor 144 may be configured to measure parameters that are indicative of the user's health or fitness level. It may be integrated into the wearable device 100 that can remain in close contact with the user's body, enabling continuous or periodic monitoring without intrusive procedures. The optical sensor 144 may also be coupled with other components in the wearable device 100 to not only collect data but also respond with appropriate bioresonance frequencies as part of a bioresonance protocol.

The bioresonance frequency emitter 146 may include an electromagnetic frequency generator, which may refer to a component or assembly that may be capable of producing and emitting electromagnetic waves at specific frequencies. The bioresonance frequency emitter 146 may be designed to create frequencies that resonate with biological processes and structures within the human body for bioresonance effect-generating purposes. It may include, for example, a power source, a circuit or a microcontroller that can be programmed or adjusted to generate electromagnetic waves at one or more predetermined frequencies. The range of frequencies may be wide and variable, allowing for customization according to various bioresonance modalities. The bioresonance frequency emitter 146 may produce and release bioresonance frequencies into the environment or towards a specific target, such as a user's body tissue. This may involve converting electrical signals into corresponding electromagnetic waves that resonate at specific frequencies associated with bioresonance effects. The act of emitting may include the propagation of these waves through the air, or, if designed accordingly, through direct contact with the skin via electrodes or other transmission elements that are part of the wearable device 100. The emission may be continuous, pulsed, modulated, or varied in intensity and duration based on the instructions received by the processor within the wearable device 100. The bioresonance frequency emitter 146 may operate within a predetermined range of frequencies that are considered to be bioactive, meaning they may in some cases have an effect on biological processes or structures when applied. The bioresonance frequency emitter 146 may include circuitry for the generation of continuous or pulsed waveforms, and it may be capable of delivering these waveforms in a manner that may be safe and effective for interaction with the user's body. The bioresonance frequency emitter 146 may also include components that ensure the stability and precision of the frequency output, such as oscillators or feedback systems, to maintain the desired frequency despite fluctuations in power supply or environmental conditions. Additionally, the electromagnetic frequency generator may be integrated with the sensors in the wearable device, enabling it to alter the output frequency in response to real-time physiological data received, such as variations in muscle temperature or blood oxygenation levels, thereby providing tailored bioresonance modalities to the user. The bioresonance frequency emitter 146 may be constructed to be compact and efficient, suitable for incorporation into a wearable device without significantly impacting the size or power consumption of the wearable device 100.

Figure 2:
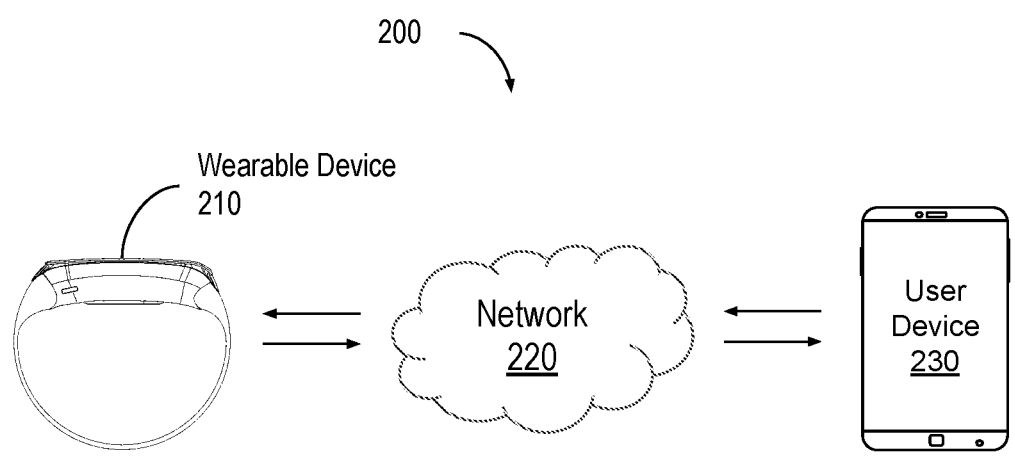
FIG. 2 illustrates a system wherein a wearable device and a user device are configured for communication and data transfer, according to one or more implementations herein.

FIG. 2 illustrates a system 200 wherein a wearable device 210 and a user device 230 are configured for communication and data transfer, according to one or more implementations herein. The wearable device 210 may comprise similar components, configurations, or capabilities to the wearable device 100, but is not limited by the description herein of the wearable device 100. Examples of the user device 230 may include smartphones, tablets, computers, dedicated health monitoring systems, or any other device equipped with processing capabilities and a network interface. The user device 230 may serve to receive physiological data transmitted by the wearable device, process this data to determine appropriate bioresonance modality instructions, and send these instructions back to the wearable device for execution. The user device 230 may also be used to input user preferences, monitor real-time data, adjust settings on the wearable device, and store historical data for trend analysis and record-keeping. Furthermore, the user device 230 may be equipped with software applications designed to enhance the functionality of the wearable device, providing a user interface for interaction with the system and enabling the download and updating of bioresonance modality instructions to its database. The communication between the wearable device 210 and the user device 230 may be established over a network 220 using various communication protocols including, for example, wired connections (e.g., USB) or wireless connections such as, for example, WIFI, BLUETOOTH, cellular networks, or near-field communication (NFC). The network 220 may include any variety of devices configured to enable a device communicate with other devices, such as via a wired connection and/or a wireless connection, for example, via the internet and/or other networks using, for example, TCP/IP or cellular hardware enabling wired or wireless (e.g., cellular, 2G, 3G, 4G, 4G LTE, 5G, or WiFi) communication. For example, the network 220 may include, inter alia, a receiver, a transmitter, a transceiver, a modem, a network interface card, and/or an antenna.

A database of bioresonance modality instructions may be stored on an electronic storage device of the user device 230 or external to the user device 230. The database may contain a variety of bioresonance modality instructions. These instructions may be used to guide the wearable device 210 in emitting specific bioresonance frequencies that correspond to various bioresonance modalities. The database may be accessed by the processor of the user device 230 to select and transmit the appropriate instructions to the wearable device 210. Additionally, the database may be configured to be updated by downloading new bioresonance modality instructions, thereby expanding the collection of frequencies that the wearable device 210 can emit. The organization of the database may be such that it supports efficient retrieval and management of the data, enabling quick response times and a streamlined user experience.

The bioresonance modality instructions may refer to a set of encoded information or commands that may be sent to, received by, or stored in the wearable device 210, in some implementations, by the user device 230. These instructions may be utilized by the processor to manage the operations of the sensors, adjust settings, execute particular functions, or control the frequency generator to emit specific bioresonance frequencies. Instructions may be pre-programmed into the wearable device 210 or may be received from an external source, such as a user device 230, as downloadable bioresonance modality instructions. They may be in the form of software updates, configuration parameters, or bioresonance protocols tailored to the user's physiological data.

Instructions may also include directives to alter the bioresonance frequency in real-time based on the sensor inputs, such as changes in muscle temperature or blood oxygen levels, to provide a customized bioresonance response. Such bioresonance modality instructions need not be fixed and can be obtained from an external source, such as a server or cloud-based service, via a network, for example, by the user device 230. Once received by the user device 230, the instructions can be transmitted to and executed by the wearable device 210 to provide a customized bioresonance session. These instructions may be designed for specific conditions and hence may be part of a larger library of bioresonance modalities that can be selectively downloaded based on the needs or preferences of a user or recommendations of a provider. The instructions may further be capable of being updated or supplemented over time, allowing for the introduction of new bioresonance modalities or the modification of existing ones to reflect advancements in research or changes in user requirements. The downloaded instructions may enable the wearable device to dynamically adjust the bioresonance frequencies it generates, for example, based on feedback from the sensors, thereby offering personalized bioresonance modality options that can evolve with ongoing use and monitoring of the user's physiological responses.

Figure 3:
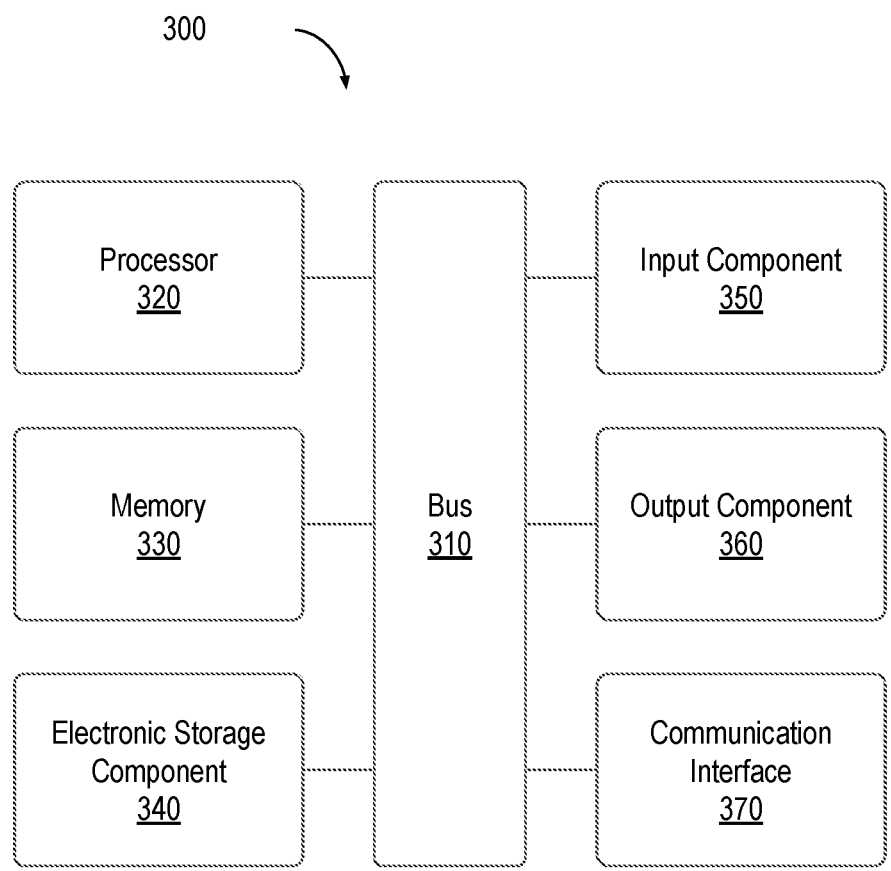
FIG. 3 is a diagram of example components of a device, according to one or more implementations herein.

FIG. 3 is a diagram of example components of a device 300, according to one or more implementations herein. The device 300 may correspond to one or more of the device(s), network(s), resource(s), or service(s) of FIG. 2. In some implementations, one or more of the device(s), network(s), resource(s), or service(s) of FIGS. 1A-2, or 4 may include one or more devices 300 and/or one or more components of device 300, for example, according to a client/server architecture, a peer-to-peer architecture, and/or other architectures, which may include a plurality of hardware, software, and/or firmware components operating together to provide the functionality attributed herein to device 300. In some implementations, device 300 may include a distributed computing architecture (e.g., one or more individual computing platforms operating in concert to accomplish a computing task). For example, device 300 may be implemented by a cloud of computing platforms operating together as device 300. By way of non-limiting example, a given device 300 may include one or more of a server, a desktop computer, a laptop computer, a handheld computer, a tablet computing platform, a Netbook, a Smartphone, a gaming console, and/or other computing platforms. The device 300 may further include a power source and/or a battery.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As shown in FIG. 3, device 300 may include a bus 310, a processor 320, a memory 330, a storage component 340, an input component 350, an output component 360, and a communication component 370.

Bus 310 includes a component that enables wired and/or wireless communication among the components of device 300.

Processor 320 includes a central processing unit, a graphics processing unit, a microprocessor, a controller, a microcontroller, a digital signal processor, a field-programmable gate array (FPGA), an application-specific integrated circuit, and/or another type of processing component. Processor 320 is implemented in hardware, firmware, or a combination of hardware and software. In some implementations, processor 320 includes one or more processors capable of being programmed to perform a function. Such processors may or may not be all integral to the same physical device, and may in some embodiments be distributed among several devices.

Processor 320 may be configured to execute one or more of the modules disclosed herein, and/or other modules by software; hardware; firmware; some combination of software, hardware, and/or firmware; and/or other mechanisms for configuring processing capabilities on processor 320. As used herein, the term "module" may refer to any component or set of components that perform the functionality attributed to the module. This may include one or more physical processors during execution of processor readable instructions, the processor readable instructions, circuitry, hardware, storage media, or any other components. Various modules or portions thereof may be implemented in any of various ways, including procedure-based techniques, component-based techniques, and/or object-oriented techniques, among others. For example, the program instructions may be implemented using system libraries, language libraries, model-view-controller (MVC) principles, application programming interfaces (APIs), system-specific programming languages and principles, cross-platform programming languages and principles, pre-compiled programming languages, markup programming languages, stylesheet languages, "bytecode" programming languages, object-oriented programming principles or languages, other programming principles or languages, C, C++, C#, Java, JavaScript, Python, PHP, HTML, CSS, TypeScript, R, Elm, Unity, VB.Net, Visual Basic, Swift, Objective-C, Perl, Ruby, Go, SQL, Haskell, Scala, Arduino, assembly language, Microsoft Foundation Classes (MFC), Streaming SIMD Extension (SSE), or other technologies or methodologies, as desired.

It should be appreciated that although some modules disclosed herein may be illustrated for example as being implemented within a single processing unit, in embodiments in which processor 320 includes multiple processing units, one or more of modules disclosed herein may be implemented remotely from the other modules. The description of the functionality provided by the different modules disclosed herein is for illustrative purposes, and is not intended to be limiting, as any of modules described herein may provide more or less functionality than is described. For example, one or more of modules disclosed herein may be eliminated, and some or all of its functionality may be provided by other ones of modules disclosed herein. As another example, processor 320 may be configured to execute one or more additional modules that may perform some or all of the functionality attributed herein to one of modules disclosed herein.

Memory 330 includes a random-access memory, a read only memory, and/or another type of memory (e.g., a flash memory, a magnetic memory, and/or an optical memory).

Electronic storage component 340 stores information and/or software related to the operation of device 300. For example, electronic storage component 340 may include a hard disk drive, a magnetic disk drive, an optical disk drive, a solid-state disk drive, a compact disc, a digital versatile disc, and/or another type of non-transitory computer-readable medium. Implementations of electronic storage component 340 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Implementations of electronic storage component 340 may include one or both of system storage provided integrally (i.e., substantially non-removable) to device 300 and/or removable storage that is removably connectable to device 300 via, for example, a port (e.g., a USB port, an IEEE 1394 port, a THUNDERBOLT port, etc.) or a drive (e.g., disk drive, flash drive, or solid-state drive etc.). Electronic storage component 340 may also or alternatively include one or more virtual storage resources (e.g., cloud storage, a virtual private network, and/or other virtual storage resources). An electronic storage may store software algorithms, information determined by one or more processors, information received from one or more computing platforms, information received from one or more remote platforms, databases (e.g., structured query language (SQL) databases (e.g., MYSQL, MARIADB, MONGODB), NO-SQL databases, among others), data files, compiled data, analyzed data, charts, tables, videos, images, presentations, and 3D content in the respective format and/or other information enabling a computing platform to function as described herein.

Input component 350 enables device 300 to receive input, such as user input and/or sensed inputs. For example, input component 350 may include a touch screen, a keyboard, a keypad, a mouse, a button, a microphone, a switch, a sensor, a global positioning system component, an accelerometer, a gyroscope, and/or an actuator.

Output component 360 enables device 300 to provide output, such as via a display, a speaker, and/or one or more light-emitting diodes.

Communication component 370 enables device 300 to communicate with other devices, such as via a wired connection and/or a wireless connection, for example, via the internet and/or other networks using, for example, TCP/IP or cellular hardware enabling wired or wireless (e.g., cellular, 2G, 3G, 4G, 4G LTE, 5G, WIFI, near field communication (NFC), BLUETOOTH) communication. For example, communication component 370 may include a receiver, a transmitter, a transceiver, a modem, a network interface card, and/or an antenna.

As used herein, "internet" may include an interconnected network of systems and a suite of protocols for the end-to-end transfer of data therebetween. A model describing may be the Transport Control Protocol and Internet Protocol (TCP/IP), which may also be referred to as the internet protocol suite. TCP/IP provides a model of four layers of abstraction: an application layer, a transport layer, an internet layer, and a link layer. The link layer may include hosts accessible without traversing a router, and thus may be determined by the configuration of the network (e.g., a hardware network implementation, a local area network, a virtual private network, or a networking tunnel). The link layer may be used to move packets of data between the internet layer interfaces of different hosts on the same link. The link layer may interface with hardware for end-to-end transmission of data. The internet layer may include the exchange of datagrams across network boundaries (e.g., from a source network to a destination network), which may be referred to as routing, and is performed using host addressing and identification over an internet protocol (IP) addressing system (e.g., IPv4, IPv6). A datagram may include a self-contained, independent, basic unit of data, including a header (e.g., including a source address, a destination address, and a type) and a payload (e.g., the data to be transported), to be transferred across a packet-switched network. The transport layer may utilize the user datagram protocol (UDP) to provide for basic data channels (e.g., via network ports) usable by applications for data exchange by establishing end-to-end, host-to-host connectivity independent of any underlying network or structure of user data. The application layer may include various user and support protocols used by applications users may use to create and exchange data, utilize services, or provide services over network connections established by the lower layers, including, for example, routing protocols, the hypertext transfer protocol (HTTP), the file transfer protocol (FTP), the simple mail transfer protocol (SMTP), and the dynamic host configuration protocol (DHCP). Such data creation and exchange in the application layer may utilize, for example, a client-server model or a peer-to-peer networking model. Data from the application layer may be encapsulated into UDP datagrams or TCP streams for interfacing with the transport layer, which may then effectuate data transfer via the lower layers.

Communication component 370 may further implement an internet-of-things ("IoT") configuration, which may include a network of physical objects-devices, vehicles, buildings, and other items-embedded with electronics, software, sensors, and network connectivity that enables these objects to collect and exchange data via the Internet. Each IoT product/device may be an endpoint device having its own Internet address (e.g., IPv4, IPV6 address). The IoT allows objects to be sensed and controlled remotely across an existing network infrastructure (e.g., the Internet), creating opportunities for more direct integration of the physical world into computer-based systems.

Device 300 may perform one or more processes described herein. For example, a non-transitory computer-readable medium (e.g., memory 330 and/or storage component 340) may store a set of instructions (e.g., one or more instructions, code, software code, and/or program code) for execution by processor 320. Processor 320 may execute the set of instructions to perform one or more processes described herein. In some implementations, execution of the set of instructions, by one or more processors 320, causes the one or more processors 320 and/or the device 300 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 3 are provided as an example. Device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

In addition to the example configuration described herein in FIG. 3, various steps, functions, and/or operations of device 300 and the methods disclosed herein may be carried out by one or more of, for example, electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random-access memory, a magnetic or optical disk, a non-volatile memory, a solid-state memory, a magnetic tape, and the like. A carrier medium may include a transmission medium such as a wire, cable, or wireless transmission link.

Figure 4:
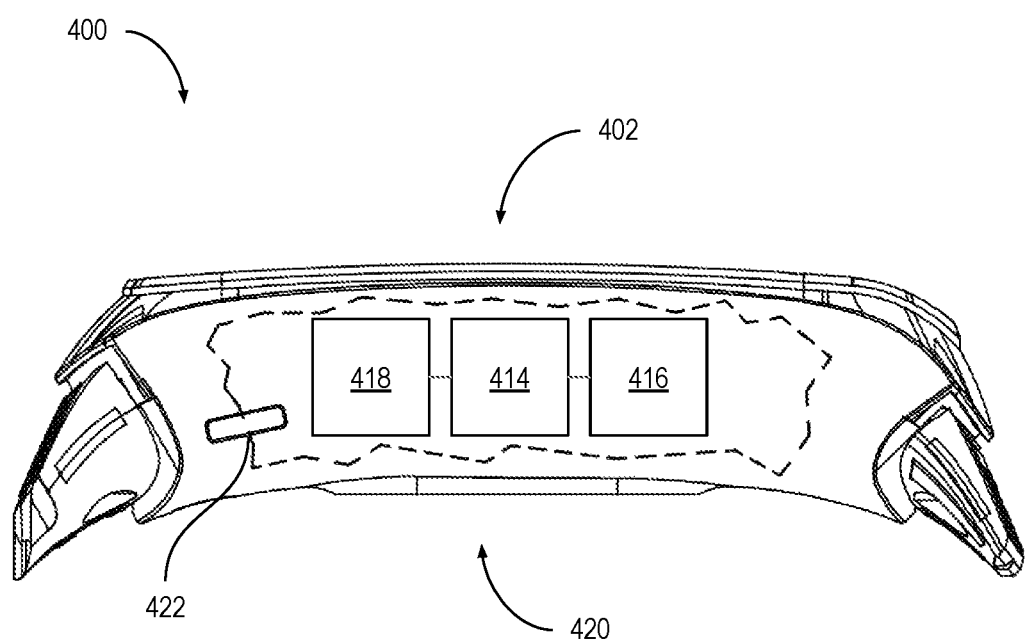
FIG. 4 illustrates example internal components of a wearable device, according to one or more implementations herein.

FIG. 4 illustrates example internal components of a wearable device 400, according to one or more implementations herein. FIG. 4 may depict the wearable device 400 in a cutaway view so as to provide visibility to the one or more processors 414, electronic storages 416, and network interfaces 418.

The wearable device 400 may be configured to communicate with other devices or remote platforms via one or more devices of FIGS. 1A-3, and/or according to a client/server architecture, a peer-to-peer architecture, and/or other architectures. The one or more processors 414, electronic storages 416, or network interfaces 418 may be in direct or indirect electronic communication with the port 422 (e.g., a USB port).

The wearable device 400 may include one or more processors 414 configured to execute computer program modules. The computer program modules may be configured to enable a user associated with the wearable device 400 to interface with a system, (e.g., similar to device 300) and/or external resources, and/or provide other functionality attributed herein to the wearable device 400.

The wearable device 400 may include the electronic storage 416, the processor 414, and/or other components. The wearable device 400 may include communication lines, or ports to enable the exchange of information with a network and/or other computing platforms (e.g., network interface 418). Illustration of the wearable device 400 in FIG. 4 is not intended to be limiting. The wearable device 400 may include a plurality of hardware, software, and/or firmware components operating together to provide the functionality attributed herein to the wearable device 400. For example, the wearable device 400 may be implemented by a cloud of computing platforms operating together as the wearable device 400.

Electronic storage 416 may be directly or indirectly in operative electronic communication with the processor 414 may comprise non-transitory storage media that electronically stores information. The electronic storage media of electronic storage 416 may include one or both of system storage that is provided integrally (i.e., substantially non-removable) with the wearable device 400 and/or removable storage that is removably connectable to the wearable device 400 via, for example, a port (e.g., a USB port, an IEEE 1394 port, a THUNDERBOLT port, etc.) or a drive (e.g., a disk drive, flash drive, or solid-state drive etc.). Electronic storage 416 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 416 may include one or more virtual storage resources (e.g., cloud storage, a virtual private network, and/or other virtual storage resources). Electronic storage 416 may store software algorithms, information determined by the processor 414, information received from the device, information received from the system or another remote platform, and/or other information that enables the wearable device 400 to function as described herein.

The processor 414 may be configured to provide information processing capabilities in the wearable device 400. As such, the processor 414 may include one or more of a digital processor, an analog processor, a digital circuit designed to process information, an analog circuit designed to process information, a state machine, and/or other mechanisms for electronically processing information. Although the processor 414 is shown in FIG. 4 as a single entity, this is for illustrative purposes only. In some embodiments, the processor 414 may include a plurality of processing units. These processing units may be physically located within the same device, or the processor 414 may represent processing functionality of a plurality of devices operating in coordination. The processor 414 may be configured to execute one or more of the modules disclosed herein, and/or other modules. The processor 414 may be configured to execute one or more of the modules disclosed herein, and/or other modules by software; hardware; firmware; some combination of software, hardware, and/or firmware; and/or other mechanisms for configuring processing capabilities on processor 414. As used herein, the term "module" may refer to any component or set of components that perform the functionality attributed to the module. This may include one or more physical processors during execution of processor readable instructions, the processor readable instructions, circuitry, hardware, storage media, or any other components. Various modules or portions thereof may be implemented in any of various ways, including procedure-based techniques, component-based techniques, and/or object-oriented techniques, among others. For example, the program instructions may be implemented using ActiveX controls, model-view-controller (MVC) principles, application programming interfaces (APIs), system-specific programming languages and principles, cross-platform programming languages and principles, pre-compiled programming languages, "byte-code" programming languages, object-oriented programming principles or languages, other programming principles or languages, JavaBeans, Microsoft Foundation Classes (MFC), Streaming SIMD Extension (SSE), or other technologies or methodologies, as desired.

It should be appreciated that although the modules disclosed herein are illustrated in FIG. 4 as being implemented within a single processing unit, in embodiments in which the processor 414 includes multiple processing units, one or more of modules disclosed herein may be implemented remotely from the other modules. The description of the functionality provided by the different modules disclosed herein is for illustrative purposes, and is not intended to be limiting, as any of modules described herein may provide more or less functionality than is described. For example, one or more of modules disclosed herein may be eliminated, and some or all of its functionality may be provided by other ones of modules disclosed herein. As another example, the processor 414 may be configured to execute one or more additional modules that may perform some or all of the functionality attributed herein to one of modules disclosed herein.

The wearable device 400 may be configured by machine-readable instructions. Such machine-readable instructions may include one or more instruction modules. The instruction modules may include computer program modules, which may be similar to, for example, at least a portion of the methods described herein. The instruction modules may include one or more of the modules and methods disclosed herein and/or other instruction modules and methods.

A network interface 418 may be directly or indirectly in operative electronic communication with, inter alia, processor 414. Network interface 418 may operatively link the processor 414 and/or the wearable device 400 with one or more other computing platform(s), remote platform(s), and/or external resources via one or more electronic communication links. For example, such electronic communication links may be established, at least in part, via a network such as the internet and/or other networks using, for example, TCP/IP or cellular hardware enabling wired or wireless (e.g., cellular, 2G, 3G, 4G, 4G LTE, 5G, WIFI, BLUETOOTH, or NFC) communication. It will be appreciated that this is not intended to be limiting, and that the scope of this disclosure includes embodiments in which the wearable device 400, one or more other computing platform(s), remote platform(s), and/or external resources may be operatively linked via some other communication media.

The processor 414 may be directly or indirectly in operative electronic communication with a display, which may be disposed on or proximate a top face 402 of the wearable device 400. The display may include a device (or "hardware component") that displays "display data" to form an image or images, such as, but not limited to, a picture, text, a desktop background, a gaming background, a video, an application window etc. One example of the display may include an integrated display as found in electronic devices such as handheld computing devices, electronic book readers, mobile telephones (smartphones), personal-digital-assistants (PDAs), wearable devices (smart-watches, smart-glasses, etc.). The display may employ any appropriate display technology, such as for example, LCD flat panel, LED flat panel, flexible-panels, etc., and may include other display hardware that may, as needed for a particular electronic device, be operatively coupled to other devices and components. Therefore, the display may include display hardware such as, but not limited to, a frame buffer, hardware display drivers, etc. that store and refresh display data to be displayed by the display. Also, the display may include integrated hardware for implementation of touchscreen functionality such that the display is operative to receive user input by touch or via a stylus.

The term "image" as used herein may refer generally to what is "displayed" on a display and which may be stored in memory as "display data." That is, an image may be displayed on a display by sending the appropriate display data to the display. Examples of images may include, but are not limited to, a background or "wallpaper," a gaming background, a video, an application window, an icon, a widget, etc. In other words, the term "image" may refer to a background, or may refer individually, or collectively, to elements or objects in the foreground hovering over a background image such as wallpaper. The term "display data" may be used interchangeably herein with the term "image data" and refers to the information (data, or digital information) that the display interprets and/or decodes to show (i.e., to display) the user an image, as well as any associated elements or objects in the foreground of the background or wallpaper, etc.

The processor 414 may be directly or indirectly in operative electronic communication with one or more sensors or emitters disposed on or proximate a bottom face 420 of the wearable device 400.

Figure 5:
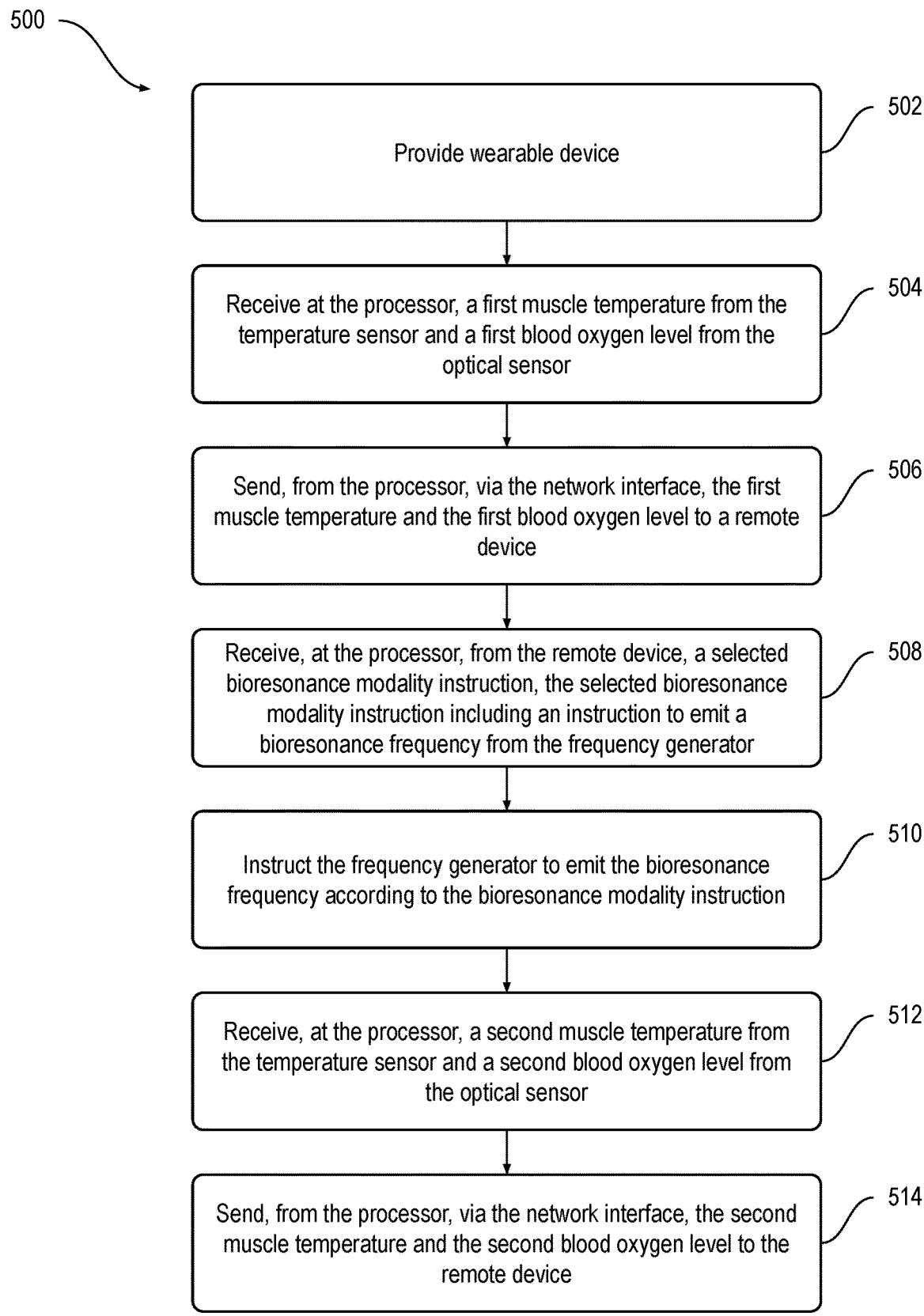
FIG. 5 is a flowchart illustrating an example method, according to one or more implementations herein.

FIG. 5 is a flowchart illustrating an example method 500, according to one or more implementations herein. In some implementations, one or more process blocks of FIG. 5 may be performed by a one or more of the wearable device 100, the wearable device 210, the network 220, the user device 230, the device 300, wearable the wearable device 400, or other devices, components, or subcomponents depicted in FIGS. 1A-4, or another device or a group of devices separate from the same.

An operation 502 may include providing a wearable device configured to be worn by a user, the wearable device including: a housing having disposed therein: a processor, a network interface in electronic communication with the processor, a temperature sensor in electronic communication with the processor and configured to sense a muscle temperature, an optical sensor in electronic communication with the processor and configured to sense a blood oxygen level, and a frequency generator in electronic communication with the processor; and a band connected to the housing and configured to removably secure the housing to the user such that the frequency generator is positioned to act on the user, and may be performed alone or in combination with one or more other operations depicted in FIG. 5.

An operation 504 may include receiving, at the processor, a first muscle temperature from the temperature sensor and a first blood oxygen level from the optical sensor, and may be performed alone or in combination with one or more other operations depicted in FIG. 5.

An operation 506 may include sending, from the processor, via the network interface, the first muscle temperature and the first blood oxygen level to a remote device, and may be performed alone or in combination with one or more other operations depicted in FIG. 5.

An operation 508 may include receiving, at the processor, from the remote device, a selected bioresonance modality instruction, the selected bioresonance modality instruction including an instruction to emit a bioresonance frequency from the frequency generator, and may be performed alone or in combination with one or more other operations depicted in FIG. 5.

An operation 510 may include instructing the frequency generator to emit the bioresonance frequency according to the bioresonance modality instruction, and may be performed alone or in combination with one or more other operations depicted in FIG. 5.

An operation 512 may include receiving, at the processor, a second muscle temperature from the temperature sensor and a second blood oxygen level from the optical sensor, and may be performed alone or in combination with one or more other operations depicted in FIG. 5.

An operation 514 may include sending, from the processor, via the network interface, the second muscle temperature and the second blood oxygen level to the remote device, and may be performed alone or in combination with one or more other operations depicted in FIG. 5.

Although FIG. 5 depicts example method 500 and operations thereof, in some implementations, a method illustrated herein may include additional operations, fewer operations, differently arranged operations, or different operations than the operations depicted in FIG. 5. Moreover, or in the alternative, two or more of the operations depicted in FIG. 5 may be performed at least partially in parallel.

Various characteristics, advantages, implementations, embodiments, and/or examples relating to the invention have been described in the foregoing description with reference to the accompanying drawings. However, the above description and drawings are illustrative only. The invention is not limited to the illustrated implementations, embodiments, and/or examples, and all implementations, embodiments, and/or examples of the invention need not necessarily achieve every advantage or purpose, or possess every characteristic, identified herein. Accordingly, various changes, modifications, or omissions may be effected by one skilled in the art without departing from the scope or spirit of the invention, which is limited only by the appended claims. Although example materials and dimensions have been provided, the invention is not limited to such materials or dimensions unless specifically required by the language of a claim. Elements and uses of the above-described implementations, embodiments, and/or examples can be rearranged and combined in manners other than specifically described above, with any and all permutations within the scope of the invention, as limited only by the appended claims.

In the claims, various portions may be prefaced with letter or number references for convenience. However, use of such references does not imply a temporal or ordered relationship not otherwise required by the language of the claims. Unless the phrase 'means for' or 'step for' appears in a particular claim or claim limitation, such claim or claim limitation should not be interpreted to invoke 35 U.S.C. § 110(f).

As used herein, satisfying a threshold may, depending on the context, refer to a value being greater than the threshold, greater than or equal to the threshold, less than the threshold, less than or equal to the threshold, equal to the threshold, and/or the like, depending on the context.

As used in the specification and in the claims, use of "and" to join elements in a list forms a group of all elements of the list. For example, a list described as comprising A, B, and C defines a list that includes A, includes B, and includes C. As used in the specification and in the claims, use of "or" to join elements in a list forms a group of at least one element of the list. For example, a list described as comprising A, B, or C defines a list that may include A, may include B, may include C, may include any subset of A, B, and C, or may include A, B, and C. Unless otherwise stated, lists herein are inclusive, that is, lists are not limited to the stated elements and may be combined with other elements not specifically stated in a list. As used in the specification and in the claims, the singular form of 'a', 'an', and 'the' include plural referents (e.g., one or more of the referent) unless the context clearly dictates otherwise.

It is to be expressly understood that the drawings are for the purpose of illustration and description only and are not intended as a definition of the limits of the invention.

It is to be expressly understood that the drawings are for the purpose of illustration and description only and are not intended as a definition of the limits of the invention.

Unless otherwise stated, any range of values disclosed herein sets out a lower limit value and an upper limit value, and such ranges include all values and ranges between and including the limit values of the stated range, and all values and ranges substantially within the stated range as defined by the order of magnitude of the stated range.

The inventors hereby state their intent to rely on the Doctrine of Equivalents to determine and assess the reasonably fair scope of their invention as pertains to any apparatus not materially departing from but outside the literal scope of the invention as set out in the following claims.

I claim:

1. A system, comprising:
   a wearable device configured to be worn by a user, the wearable device including:
      a housing having disposed therein:
         a processor,
         a network interface in electronic communication with the processor,
         a temperature sensor in electronic communication with the processor and configured to sense a muscle temperature,
         an optical sensor in electronic communication with the processor and configured to sense a blood oxygen level, and
         an electromagnetic frequency generator in electronic communication with the processor; and
      a band connected to the housing and configured to removably secure the housing to the user such that the electromagnetic frequency generator is positioned to act on the user;
   wherein the processor is configured to:
      receive a first muscle temperature from the temperature sensor and a first blood oxygen level from the optical sensor;
      send, via the network interface, the first muscle temperature and the first blood oxygen level to a remote device;
      receive, from the remote device, a selected bioresonance modality instruction, the selected bioresonance modality instruction including an instruction to emit an electromagnetic bioresonance frequency from the electromagnetic frequency generator;
      instruct the electromagnetic frequency generator to emit the electromagnetic bioresonance frequency according to the selected bioresonance modality instruction;
      receive a second muscle temperature from the temperature sensor and a second blood oxygen level from the optical sensor; and
      send, via the network interface, the second muscle temperature and the second blood oxygen level to the remote device.

2. The system of claim 1, wherein the wearable device is configured to be worn on a wrist of the user.

3. The system of claim 1, wherein the wearable device is configured to be worn on an ankle of the user.

4. The system of claim 1, wherein the network interface is a BLUETOOTH network interface.

5. The system of claim 1, wherein the remote device comprises an electronic storage device having a database stored thereon, the database comprising a plurality of bioresonance modality instructions including the selected bioresonance modality instruction.

6. The system of claim 5, wherein the selected bioresonance modality instruction is selected on the remote device from the plurality of bioresonance modality instructions.

7. The system of claim 5, wherein the remote device is configured to download a downloadable bioresonance modality instruction and add the downloadable bioresonance modality instruction to the plurality of bioresonance modality instructions.

8. The system of claim 1, wherein the processor is further configured to change the electromagnetic bioresonance frequency based on one or more of the first muscle temperature, the second muscle temperature, the first blood oxygen level, or the second blood oxygen level.

9. A method, comprising:
   providing a wearable device configured to be worn by a user, the wearable device including:
      a housing having disposed therein:
         a processor,
         a network interface in electronic communication with the processor, a temperature sensor in electronic communication with the processor and configured to sense a muscle temperature,
an optical sensor in electronic communication with the processor and configured to sense a blood oxygen level, and
a frequency generator in electronic communication with the processor; and
a band connected to the housing and configured to removably secure the housing to the user such that the frequency generator is positioned to act on the user;
receiving, at the processor, a first muscle temperature from the temperature sensor and a first blood oxygen level from the optical sensor;
sending, from the processor, via the network interface, the first muscle temperature and the first blood oxygen level to a remote device;
receiving, at the processor, from the remote device, a selected bioresonance modality instruction, the selected bioresonance modality instruction including an instruction to emit a bioresonance frequency from the frequency generator;
instructing the frequency generator to emit the bioresonance frequency according to the selected bioresonance modality instruction;
receiving, at the processor, a second muscle temperature from the temperature sensor and a second blood oxygen level from the optical sensor; and
sending, from the processor, via the network interface, the second muscle temperature and the second blood oxygen level to the remote device.

10. The method of claim 9, wherein the frequency generator is an electromagnetic frequency generator and the bioresonance frequency is an electromagnetic frequency.

11. The method of claim 9, wherein the wearable device is configured to be worn on a wrist or an ankle of the user.

12. The method of claim 9, wherein the network interface is a BLUETOOTH network interface.

13. A system, comprising:
a wearable device, the wearable device including:
a housing having disposed therein:
a processor,
a network interface in electronic communication with the processor,
a temperature sensor in electronic communication with the processor and configured to sense a muscle temperature,
an optical sensor in electronic communication with the processor and configured to sense a blood oxygen level, and
a frequency generator in electronic communication with the processor;
wherein the processor is configured to:
receive a first muscle temperature from the temperature sensor and a first blood oxygen level from the optical sensor;
send, via the network interface, the first muscle temperature and the first blood oxygen level to a remote device;
receive, from the remote device, a selected bioresonance modality instruction, the selected bioresonance modality instruction including an instruction to emit a bioresonance frequency from the frequency generator; and
instruct the frequency generator to emit the bioresonance frequency according to the selected bioresonance modality instruction.

14. The system of claim 13, wherein the processor is further configured to:
receive a second muscle temperature from the temperature sensor and a second blood oxygen level from the optical sensor; and
send, via the network interface, the second muscle temperature and the second blood oxygen level to the remote device.

15. The system of claim 14, wherein the processor is further configured to change the bioresonance frequency based on one or more of the first muscle temperature, the second muscle temperature, the first blood oxygen level, or the second blood oxygen level.

16. The system of claim 13, wherein the wearable device further includes a band connected to the housing and configured to removably secure the housing to a user such that the frequency generator is positioned to act on the user.

17. The system of claim 13, wherein the frequency generator is an electromagnetic frequency generator and the bioresonance frequency is an electromagnetic frequency.

18. The system of claim 13, wherein the network interface is a BLUETOOTH network interface.

19. The system of claim 13, wherein the remote device comprises an electronic storage device having a database stored thereon, the database comprising a plurality of bioresonance modality instructions including the selected bioresonance modality instruction.

20. The system of claim 19, wherein the selected bioresonance modality instruction is selected on the remote device from the plurality of bioresonance modality instructions.

* * * * *